(12) United States Patent
Koblish

(10) Patent No.: US 6,745,080 B2
(45) Date of Patent: Jun. 1, 2004

(54) HELICAL AND PRE-ORIENTED LOOP STRUCTURES FOR SUPPORTING DIAGNOSTIC AND THERAPEUTIC ELEMENTS IN CONTACT WITH BODY TISSUE

(75) Inventor: Josef V. Koblish, Palo Alto, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 82 days.

(21) Appl. No.: 09/832,612

(22) Filed: Apr. 10, 2001

(65) Prior Publication Data

US 2001/0020174 A1 Sep. 6, 2001

Related U.S. Application Data

(63) Continuation-in-part of application No. 09/447,186, filed on Nov. 22, 1999, now Pat. No. 6,542,781.

(51) Int. Cl.⁷ ................................. A61N 1/00
(52) U.S. Cl. ................................. 607/122
(58) Field of Search .............. 604/20–21, 104–109, 604/523, 524, 525, 530, 532; 607/115, 119–123, 126–128; 600/372–374; 606/198

(56) References Cited

U.S. PATENT DOCUMENTS

| | | | | |
|---|---|---|---|---|
| 4,419,094 A | * | 12/1983 | Patel | 604/93 |
| 4,650,466 A | | 3/1987 | Luther | |
| 4,706,671 A | * | 11/1987 | Weinrib | 128/348.1 |
| 4,834,724 A | * | 5/1989 | Geiss et al. | 604/280 |
| 4,921,484 A | | 5/1990 | Hillstead | |
| 5,016,808 A | | 5/1991 | Heil, Jr. | |
| 5,054,501 A | * | 10/1991 | Chuttani et al. | 128/772 |
| 5,163,431 A | * | 11/1992 | Griep | 128/658 |
| 5,228,442 A | | 7/1993 | Imran | |
| 5,239,999 A | | 8/1993 | Imran | |
| 5,279,299 A | | 1/1994 | Imran | |
| 5,411,546 A | | 5/1995 | Bowald | |
| 5,456,667 A | | 10/1995 | Ham | |
| 5,545,200 A | | 8/1996 | West | |
| 5,549,661 A | | 8/1996 | Kordis | |
| 5,582,609 A | | 12/1996 | Swanson | |
| 5,716,410 A | * | 2/1998 | Wang et al. | 623/12 |
| 5,722,401 A | | 3/1998 | Pietroski | |
| 5,755,760 A | | 5/1998 | Maguire | |
| 5,814,028 A | | 9/1998 | Swartz | |
| 5,836,925 A | * | 11/1998 | Soltesz | 604/280 |
| 5,836,947 A | | 11/1998 | Fleischman | |
| 5,860,974 A | | 1/1999 | Abele | |

(List continued on next page.)

FOREIGN PATENT DOCUMENTS

| | | |
|---|---|---|
| EP | 0868922 A2 | 10/1998 |
| EP | 1042990 A1 | 10/2000 |
| WO | wo98/26724 | 6/1998 |
| WO | wo99/02096 | 1/1999 |
| WO | wo99/18878 | 4/1999 |
| WO | wo99/34741 | 7/1999 |
| WO | wo00/01313 | 1/2000 |
| WO | WO 01/37723 A2 | 5/2001 |

OTHER PUBLICATIONS

PCT Search Report dated Aug. 13, 2002 for PCT App. Ser. No. PCT/US02/08899.
U.S. application Ser. No. 09/447,186, filed Nov. 22, 1999 (atty. docket No. 15916–258).
U.S. application Ser. No. 09/447,185, filed Nov. 22, 1999 (atty. docket No. 15916–262).
US Pat. Pub No. 2001/0020174A1.

*Primary Examiner*—Sharon Kennedy
(74) *Attorney, Agent, or Firm*—Henricks, Slavin & Holmes LLP

(57) ABSTRACT

A probe that facilitates the creation of circumferential lesions in body tissue. The probe includes a probe body and a helical or loop structure that supports electrodes or other operative elements against the body tissue.

39 Claims, 14 Drawing Sheets

U.S. PATENT DOCUMENTS

| | | |
|---|---|---|
| 5,879,295 A | 3/1999 | Li |
| 5,891,112 A * | 4/1999 | Samson ............... 604/282 |
| 5,938,660 A | 8/1999 | Swartz |
| 5,938,694 A | 8/1999 | Jaraczewski |
| 5,971,983 A | 10/1999 | Lesh |
| 5,972,019 A | 10/1999 | Engelson |
| 6,012,457 A | 1/2000 | Lesh |
| 6,016,809 A | 1/2000 | Mulier |
| 6,024,740 A | 2/2000 | Lesh |
| 6,064,902 A | 5/2000 | Haissaguerre |
| 6,071,274 A | 6/2000 | Thompson |
| 6,071,279 A | 6/2000 | Whayne |
| 6,071,281 A | 6/2000 | Burnside |
| 6,106,522 A | 8/2000 | Fleischman |
| 6,117,101 A | 9/2000 | Diederich |
| 6,152,920 A | 11/2000 | Thompson |
| 6,203,525 B1 | 3/2001 | Whayne |
| 6,233,491 B1 | 5/2001 | Kordis |
| 6,280,441 B1 | 8/2001 | Ryan |
| 6,325,797 B1 | 12/2001 | Stewart |
| 6,371,928 B1 * | 4/2002 | Mcfann et al. ............... 600/585 |
| 6,391,018 B1 * | 5/2002 | Tanaka et al. ............... 604/524 |
| 2001/0007070 A1 | 7/2001 | Stewart |
| 2002/0004644 A1 | 1/2002 | Koblish |

* cited by examiner

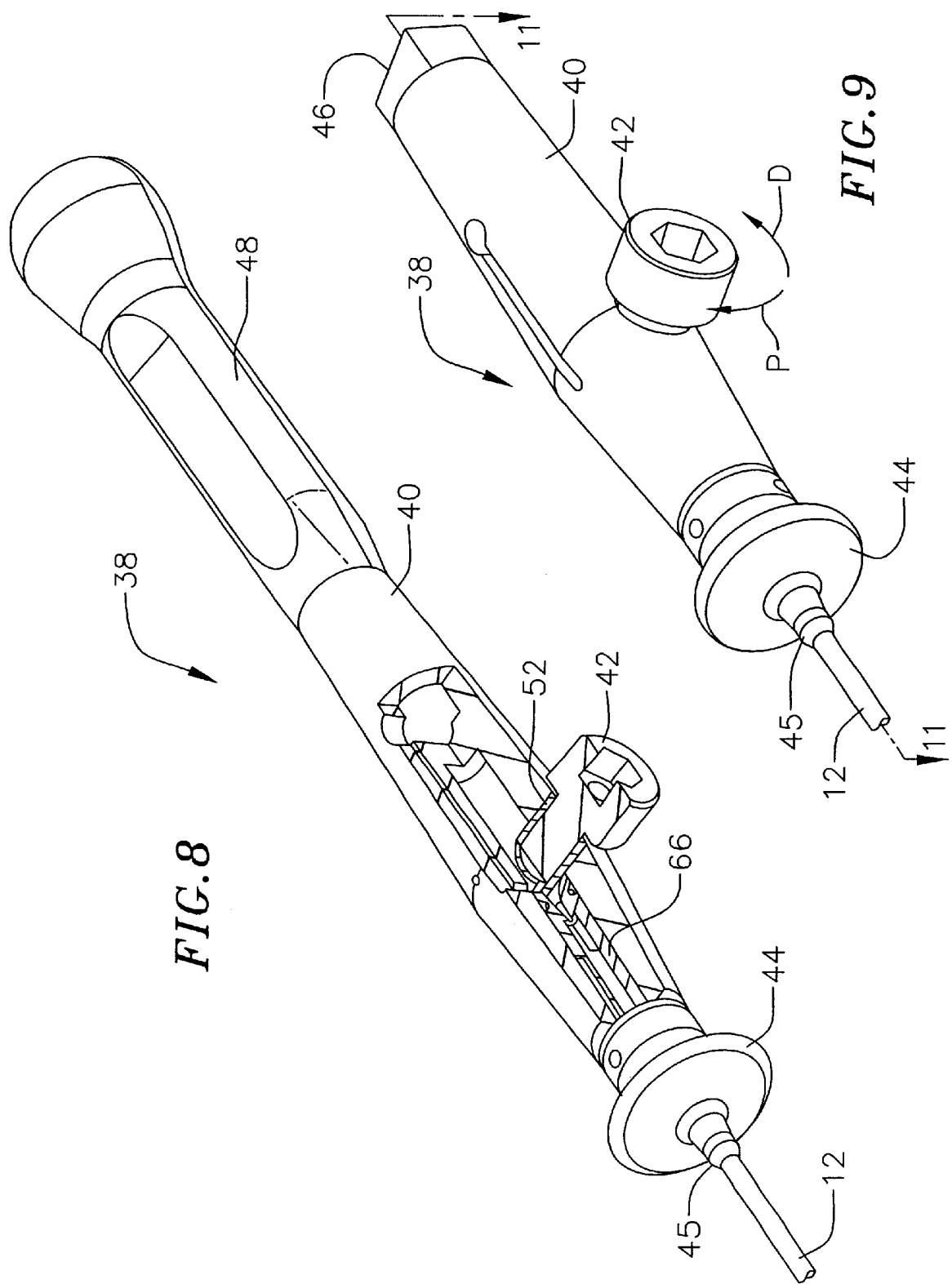

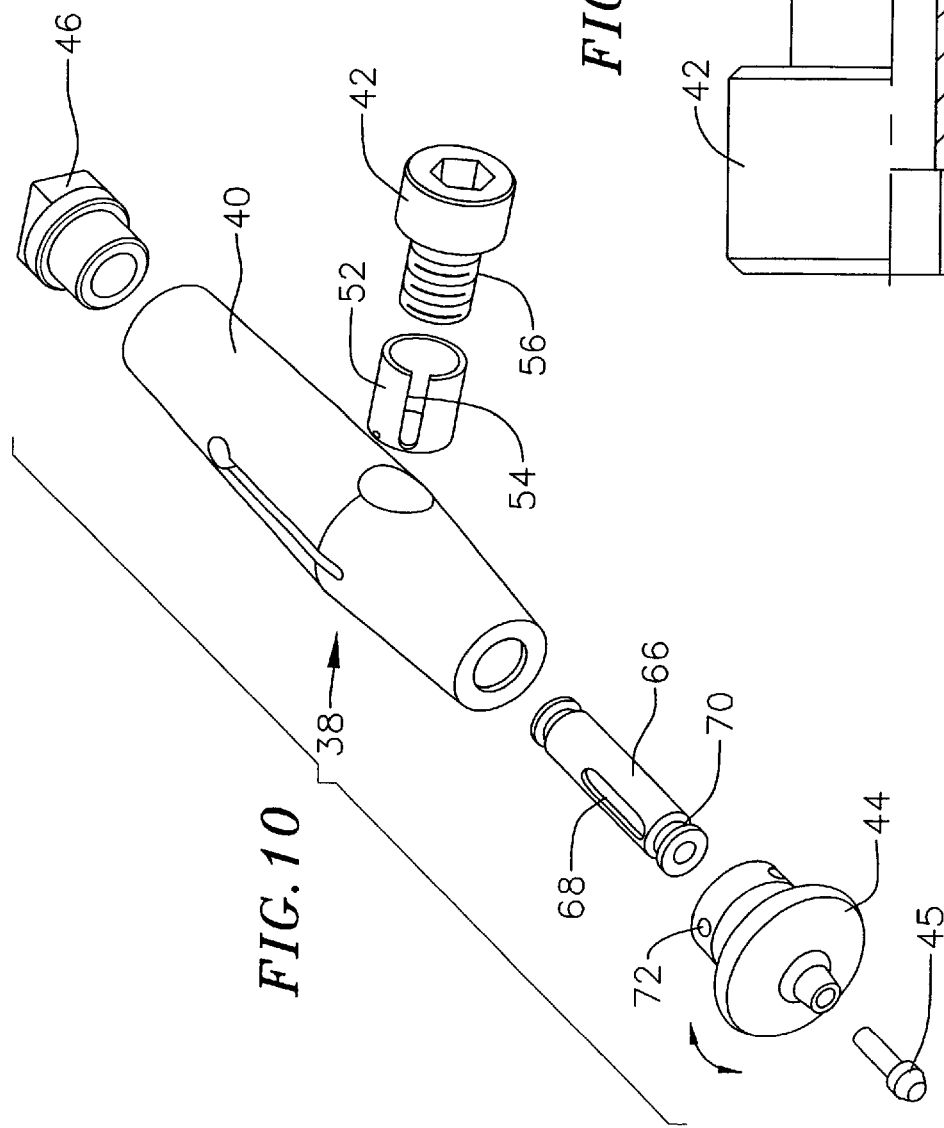
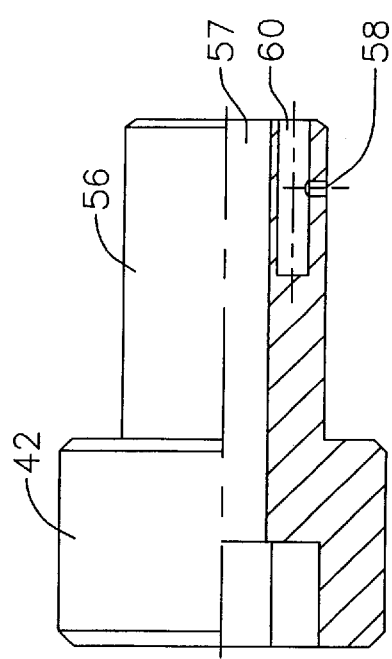

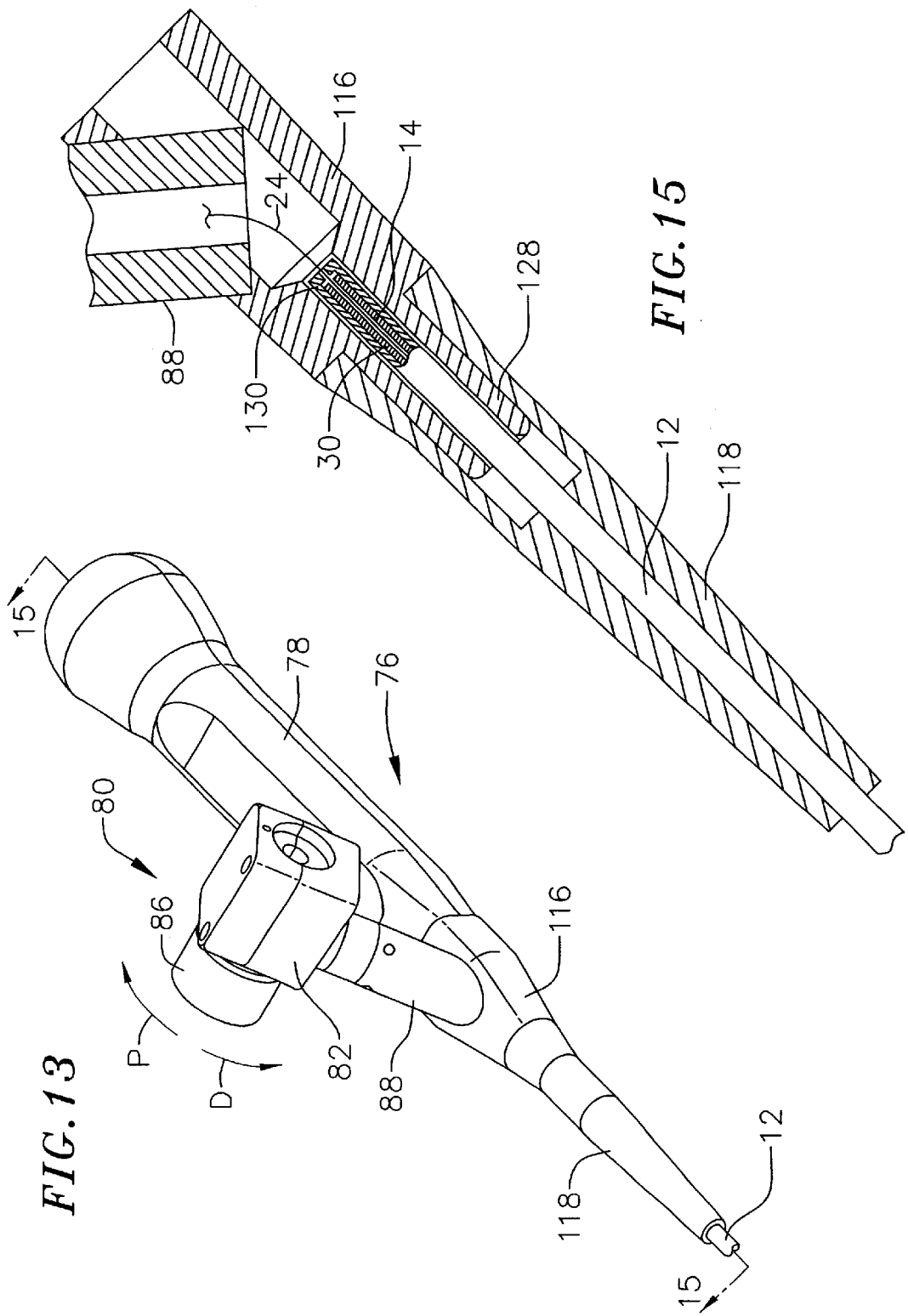

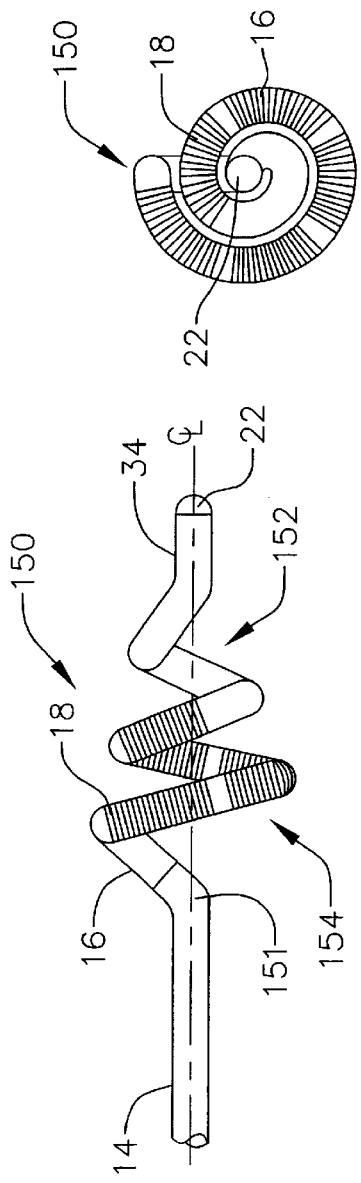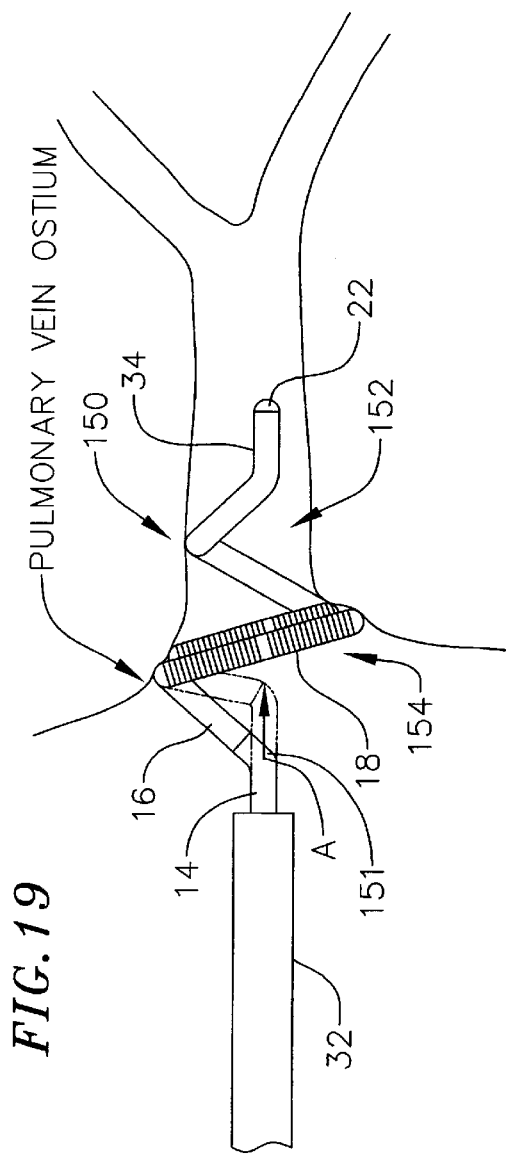

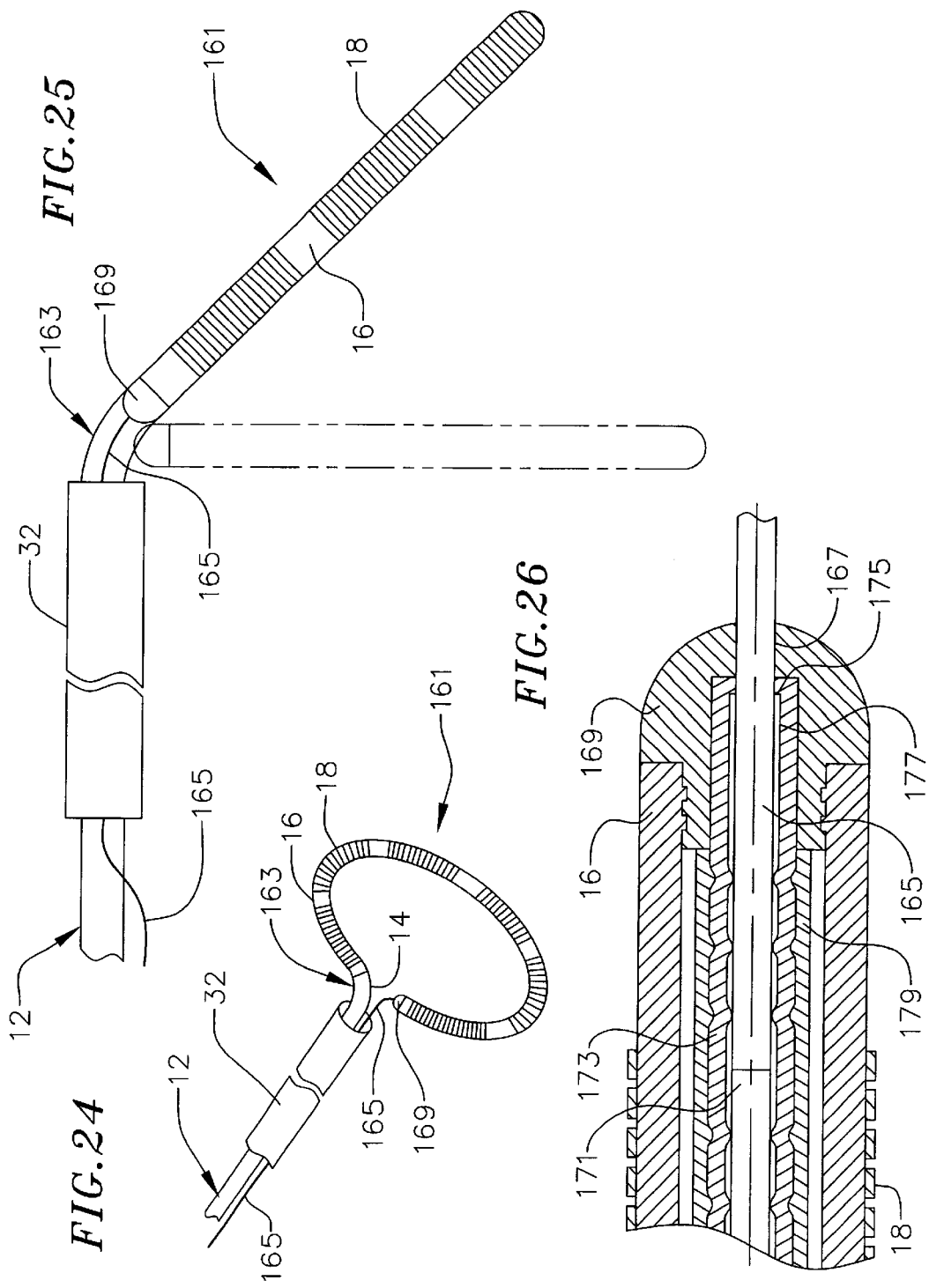

HELICAL AND PRE-ORIENTED LOOP STRUCTURES FOR SUPPORTING DIAGNOSTIC AND THERAPEUTIC ELEMENTS IN CONTACT WITH BODY TISSUE

CROSS-REFERENCE TO RELATED APPLICATIONS

This application is a continuation-in-part of U.S. application Ser. No. 09/447,186, filed Nov. 22, 1999, now U.S. Pat. No. 6,542,781, issued Apr. 1, 2003.

BACKGROUND OF THE INVENTIONS

1. Field of Inventions

The present invention relates generally to medical devices that support one or more diagnostic or therapeutic elements in contact with body tissue and, more particularly, to medical devices that support one or more diagnostic or therapeutic elements in contact with bodily orifices or the tissue surrounding such orifices.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive.

Maze-like procedures have also been developed utilizing catheters which can form lesions on the endocardium (the lesions being 1 to 15 cm in length and of varying shape) to effectively create a maze for electrical conduction in a predetermined path. The formation of these lesions by soft tissue coagulation (also referred to as "ablation") can provide the same therapeutic benefits that the complex incision patterns that the surgical maze procedure presently provides, but without invasive, open heart surgery.

Catheters used to create lesions typically include a relatively long and relatively flexible body portion that has a soft tissue coagulation electrode on its distal end and/or a series of spaced tissue coagulation electrodes near the distal end. The portion of the catheter body portion that is inserted into the patient is typically from 23 to 55 inches in length and there may be another 8 to 15 inches, including a handle, outside the patient. The length and flexibility of the catheter body allow the catheter to be inserted into a main vein or artery (typically the femoral artery), directed into the interior of the heart, and then manipulated such that the coagulation electrode contacts the tissue that is to be ablated. Fluoroscopic imaging is used to provide the physician with a visual indication of the location of the catheter.

In some instances, the proximal end of the catheter body is connected to a handle that includes steering controls. Exemplary catheters of this type are disclosed in U.S. Pat. No. 5,582,609. In other instances, the catheter body is inserted into the patient through a sheath and the distal portion of the catheter is bent into loop that extends outwardly from the sheath. This may be accomplished by pivotably securing the distal end of the catheter to the distal end of the sheath, as is illustrated in U.S. Pat. No. 6,071,279. The loop is formed as the catheter is pushed in the distal direction. The loop may also be formed by securing a pull wire to the distal end of the catheter that extends back through the sheath, as is illustrated in U.S. Pat. No. 6,048,329, which is incorporated herein by reference. Loop catheters are advantageous in that they tend to conform to different tissue contours and geometries and provide intimate contact between the spaced tissue coagulation electrodes (or other diagnostic or therapeutic elements) and the tissue.

One lesion that has proven to be difficult to form with conventional devices is the circumferential lesion that is used to isolate the pulmonary vein and cure ectopic atrial fibrillation. Lesions that isolate the pulmonary vein may be formed within the pulmonary vein itself or in the tissue surrounding the pulmonary vein. Conventional steerable catheters and loop catheters have proven to be less than effective with respect to the formation of such circumferential lesions. Specifically, it is difficult to form an effective circumferential lesion by forming a pattern of relatively small diameter lesions. More recently, inflatable balloon-like devices that can be expanded within or adjacent to the pulmonary vein have been introduced. Although the balloon-like devices are generally useful for creating circumferential lesions, the inventors herein have determined that these devices have the undesirable effect of occluding blood flow through the pulmonary vein.

Accordingly, the inventors herein have determined that a need exists generally for structures that can be used to create circumferential lesions within or around bodily orifices without occluding fluid flow and, in the context of the treatment of atrial fibrillation, within or around the pulmonary vein without occluding blood flow.

SUMMARY OF THE INVENTION

Accordingly, the general object of the present inventions is to provide a device that avoids, for practical purposes, the aforementioned problems. In particular, one object of the present inventions is to provide a device that can be used to create circumferential lesions in or around the pulmonary vein and other bodily orifices in a more efficient manner than conventional apparatus. Another object of the present invention is to provide a device that can be used to create circumferential lesions in or around the pulmonary vein and other bodily orifices without occluding blood or other bodily fluid flow.

In order to accomplish some of these and other objectives, a probe in accordance with one embodiment of a present invention includes a probe body and a helical structure associated with the distal region of the probe body. In one implementation, a plurality of spaced electrodes are carried by the helical structure. Such a probe provides a number of advantages over conventional apparatus. For example, the helical structure can be readily positioned within the body such that a ring of electrodes is brought into contact with the tissue in or around a pulmonary vein or other bodily orifice. The helical structure also defines an opening that allows blood or other bodily fluids to pass therethrough. As a result, the present probe facilitates the formation of a circumferential lesion without the difficulties and occlusion of blood or other fluids that is associated with conventional apparatus.

In one implementation, the helical structure tapers from a larger proximal diameter down to a smaller distal diameter. The larger diameter will correspond to the pulmonary vein ostium and the smaller diameter will correspond to the interior of the pulmonary vein when the probe is designed to form lesions around a pulmonary vein. So configured, the tapered helical structure will be self-centering when inserted into a pulmonary vein because the structure will wedge itself against the pulmonary vein ostium and the internal wall of the pulmonary vein itself. This insures proper positioning of the electrodes and prevents beating related movement of the heart from the knocking the structure out of position.

The flexibility of the distal portion of the helical structure may be increased and, in some implementations, to a point where the distal portion of the tapered helical structure will be more flexible than the proximal portion. A helical structure with a more flexible distal portion will prevent tissue damage as the physician pokes around within the atrium while attempting to insert the helical structure into a pulmonary vein. The more flexible distal portion is also easily uncoiled for placement within the sheath and will be more likely to remain uncoiled, thereby limiting friction, as it slides though the sheath than will a stiffer distal portion. The stiffer proximal portion, on the other hand, allows the physician to press the electrodes against the tissue with more force so that proper tissue/electrode contact is achieved when lesions are being created.

In one implementation, the probe body and helical structure will be coaxial and arranged such that proximal end of the helical structure will be connected to the probe body by a curved portion that is pre-bent (at, for example, a 45 degree angle) relative to the longitudinal axis of the probe body. The curved portion will typically be bent out of its pre-bent orientation when the helical structure is urged against tissue. As a result, the curved portion will generate a spring force that urges the helical structure against the tissue and improves tissue/electrode contact. Additionally, because the curved portion is located along the axis of the helical structure, the spring force will be distributed evenly around the circumference of the helical structure.

In order to accomplish some of these and other objectives, a probe in accordance with one embodiment of a present invention includes a probe body defining a curved portion having a pre-set curvature and a control element defining a distal portion associated with the distal region of the probe body and extending outwardly therefrom and proximally to the proximal end of the probe body. In one preferred implementation, a plurality of spaced electrodes are carried by the distal region of the probe body and the control element may be used to pull the distal region into a loop that lies in a plane which is angled relative to the longitudinal axis of the probe body (at, for example, 45 degrees). Such a probe provides a number of advantages over conventional apparatus. For example, the curved portion will typically be bent out of its pre-bent orientation when the loop is urged against tissue. As a result, the curved portion will generate a spring force that urges the loop against the tissue and improves tissue/electrode contact.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 5b is a section view taken along line 5b—5b in FIG. 5a.

FIG. 8 is a perspective, cutaway view of a probe handle in accordance with a preferred embodiment of a present invention.

FIG. 9 is a perspective view of a portion of the probe handle illustrated in FIG. 8.

FIG. 10 is an exploded view of the portion of the probe handle illustrated in FIG. 9.

FIG. 12 is a partial section view of the knob and spool arrangement in the probe handle illustrated in FIG. 8.

FIG. 13 is a perspective view of a probe handle in accordance with a preferred embodiment of a present invention.

FIG. 15 is a partial section view taken along line 15—15 in FIG. 13.

FIG. 16b is a section view taken alone line 16b—16b in FIG. 16a.

FIG. 17 is a side view of a probe in accordance with a preferred embodiment of a present invention.

FIG. 18 is a front view of the probe illustrated in FIG. 17.

FIG. 19 is a side view showing the probe illustrated in FIG. 17 being urged against a pulmonary vein ostium.

FIG. 24 is a perspective view of a probe in accordance with a preferred embodiment of a present invention.

FIG. 25 is a side view of the probe illustrated in FIG. 24.

FIG. 26 is a side, partial section view of the distal portion of the probe illustrated in FIG. 24.

DETAILED DESCRIPTION OF THE PREFERRED EMBODIMENTS

Figure 2:
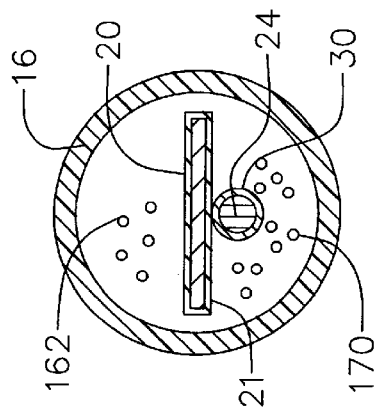
FIG. 2 is a section view taken along line 2—2 in FIG. 1.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
II. Helical Structures
III. Pre-Oriented Loop Structures
IV. Electrodes, Temperature Sensing and Power Control The section titles and overall organization of the present detailed description are for the purpose of convenience only and are not intended to limit the present inventions.

I. Introduction

The present inventions may be used within body lumens, chambers or cavities for diagnostic or therapeutic purposes in those instances where access to interior bodily regions is obtained through, for example, the vascular system or alimentary canal and without complex invasive surgical procedures. For example, the inventions herein have application in the diagnosis and treatment of arrhythmia conditions within the heart. The inventions herein also have application in the diagnosis or treatment of ailments of the gastrointestinal tract, prostrate, brain, gall bladder, uterus, and other regions of the body.

With regard to the treatment of conditions within the heart, the present inventions are designed to produce intimate tissue contact with target substrates associated with various arrhythmias, namely atrial fibrillation, atrial flutter, and ventricular tachycardia. For example, the distal portion of a catheter in accordance with a present invention, which may include diagnostic and/or soft tissue coagulation electrodes, can be used to create lesions within or around the pulmonary vein to treat ectopic atrial fibrillation.

The structures are also adaptable for use with probes other than catheter-based probes. For example, the structures disclosed herein may be used in conjunction with hand held surgical devices (or "surgical probes"). The distal end of a surgical probe may be placed directly in contact with the targeted tissue area by a physician during a surgical procedure, such as open heart surgery. Here, access may be obtained by way of a thoracotomy, median sternotomy, or thoracostomy. Exemplary surgical probes are disclosed in U.S. Pat. No. 6,142,994.

Surgical probe devices in accordance with the present inventions preferably include a handle, a relatively short shaft, and one of the distal assemblies described hereafter in the catheter context. Preferably, the length of the shaft is about 4 inches to about 18 inches. This is relatively short in comparison to the portion of a catheter body that is inserted into the patient (typically from 23 to 55 inches in length) and the additional body portion that remains outside the patient. The shaft is also relatively stiff. In other words, the shaft is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial.

II. Helical Structures

As illustrated for example in FIGS. 1–7, a catheter 10 in accordance with a preferred embodiment of a present invention includes a hollow, flexible catheter body 12 that is formed from two tubular parts, or members. The proximal member 14 is relatively long and is attached to a handle (discussed below with reference to FIGS. 8–15), while the distal member 16, which is relatively short, carries a plurality of spaced electrodes 18 or other operative elements. The proximal member 14 is typically formed from a biocompatible thermoplastic material, such as a Pebax® material (polyether block emide) and stainless steel braid composite, which has good torque transmission properties. In some implementations, an elongate guide coil (not shown) may also be provided within the proximal member 14. The distal member 16 is typically formed from a softer, more flexible biocompatible thermoplastic material such as unbraided Pebax® material, polyethylene, or polyurethane. The proximal and distal members, which are about 5 French to about 9 French in diameter, are preferably either bonded together with an overlapping thermal bond or adhesively bonded together end to end over a sleeve in what is referred to as a "butt bond."

At least a portion of the distal member 16 has a generally helical shape that defines a longitudinal axis coincident with the longitudinal axis of the remainder of the catheter. The number of revolutions (or "coils"), length, diameter, orientation and shape of the helical portion will vary from application to application. The helical portion of the distal member 16 in the embodiment illustrated in FIGS. 1–7, which may be used to create lesions in or around the pulmonary vein, revolves around the longitudinal axis of the catheter 10 one and one-half times in its relaxed state. The diameter of the helical portion can be substantially constant over its length. The diameter may, alternatively, vary over the length of the helical portion. For example, the helical portion could have a generally frusto-conical shape where the diameter decreases in the distal direction as is discussed below with reference to FIGS. 17–23.

The helical shape of the exemplary distal member 16 may be achieved through the use of a center support 20 (FIG. 2) that is positioned inside of and passes within the length of the distal member. The center support 20 is preferably a rectangular wire formed from resilient inert wire, such as Nickel Titanium (commercially available under the trade name Nitinol®)) or 17-7 stainless steel wire, with a portion thereof heat set into the desired helical configuration. The thickness of the rectangular center support 20 is preferably between about 0.010 inch and about 0.015 inch. Resilient injection molded plastic can also be used. Although other cross sectional configurations can be used, such as a round wire, a rectangular cross section arranged such that the longer edge extends in the longitudinal direction is preferred for at least the helical portion. Such an orientation reduces the amount of torsional force, as compared to a round wire, required to unwind the helical portion into an expanded configuration and collapse the helical portion into a circular structure in the manner described below. The preferred orientation of the center support 20 also increases the stiffness of the helical portion in the longitudinal direction, which allows the physician to firmly press the present structure against tissue. The center support 20 is also preferably housed in an insulative tube 21 formed from material such as Teflon™ or polyester.

In the illustrated embodiment, the proximal end of the helical center support 20 is secured to a C-shaped crimp sleeve (not shown) that is located where the proximal and distal members 14 and 16 are bonded to one another and is mounted on a guide coil (not shown) which extends through the proximal member 14 to the distal end thereof. The distal end of the guide coil is located in the area where the proximal and distal members 14 and 16 are bonded to one another. This bond also anchors the proximal end of the center support 20 to the distal end of the proximal member 14. The distal end of the center support 20 is secured to a tip member 22 which is in turn secured to the distal end of the distal member 16 with adhesive. Additional details concerning the placement of a center support within the distal member of a catheter can be found in commonly assigned U.S. patent application Ser. No. 09/150,833, entitled "Catheter Having Improved Torque Transmission Capability and Method of Making the Same," which is incorporated herein by reference.

Figure 1:
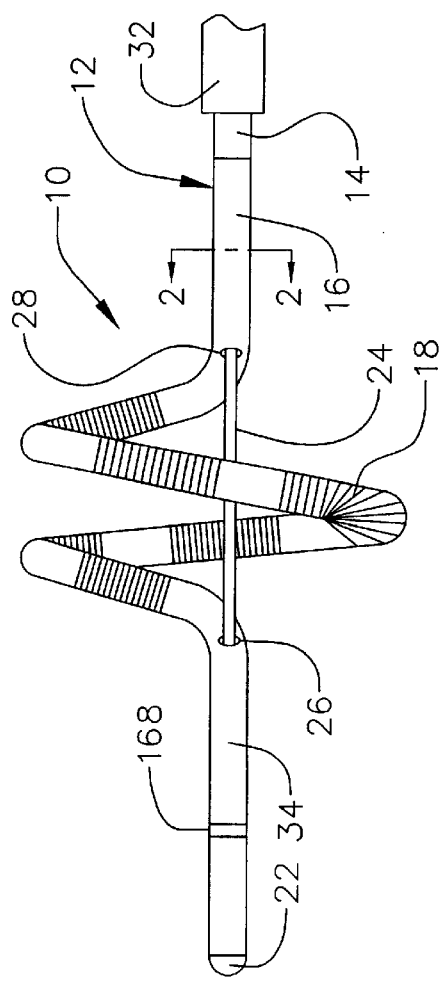
FIG. 1 is a side view of a probe in a relaxed state in accordance with a preferred embodiment of a present invention.
Figure 3:
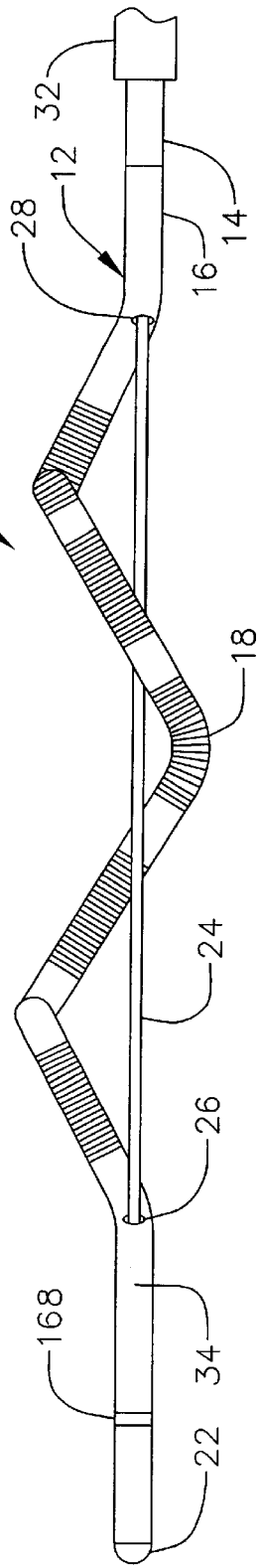
FIG. 3 is a side view of the probe illustrated in FIG. 1 with the stylet extended.
Figure 4:
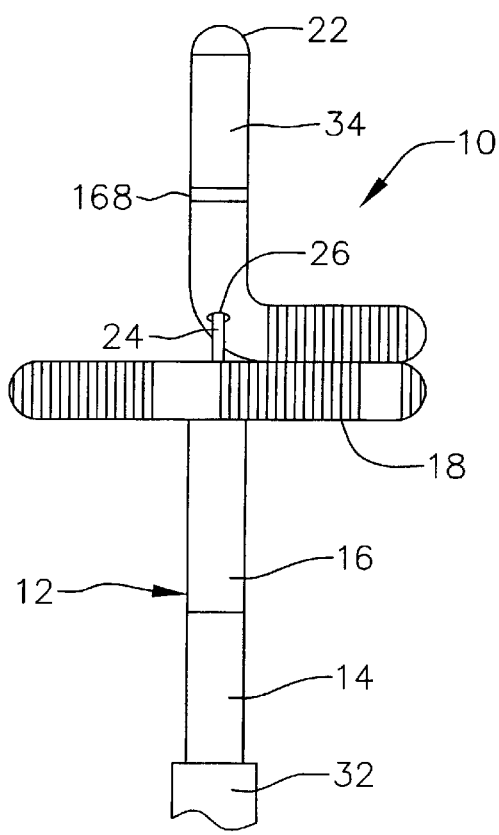
FIG. 4 is a side view of the probe illustrated in FIG. 1 with the stylet retracted.
Figure 7:
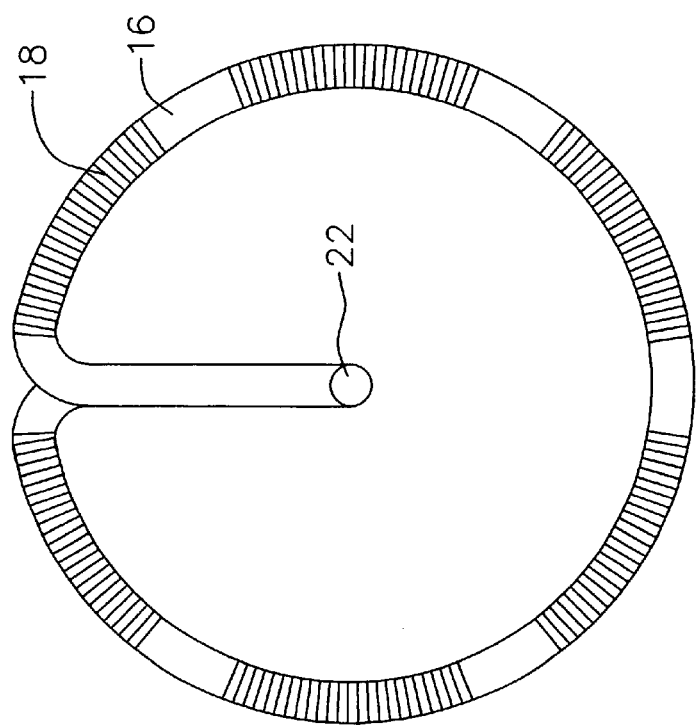
FIG. 7 is an end view of the probe illustrated in FIG. 6.

The exemplary catheter 10 also includes a stylet 24 that enables the physician to manipulate the helical portion of the distal member 16 and adjust its shape from the at rest shape illustrated in FIG. 1. For example, the stylet 24 can be moved distally to deform the helical portion of the distal member 16 in the manner illustrated in FIG. 3 or proximally to deform the helical portion in the manner illustrated in FIGS. 4–5b. The physician can also rotate the stylet 24 in one direction, which will cause the helical portion of the distal member 16 to unwind and so that its diameter increases, as illustrated in FIGS. 6 and 7, or rotate the stylet in the other direction to cause the distal member to wind up and its diameter to decrease.

In any of these states, the helical portion will define an open area interior to the electrodes 18 through which blood or other bodily fluids can flow. As a result, the helical portion can be used to create a circumferential lesion in or around the pulmonary vein, or other bodily orifice, without occluding fluid flow.

The stylet 24, which is preferably formed from inert wire such as Nitinol® or 17-7 stainless steel wire and should be stiffer than the center support 20, extends through the catheter body 12 from the proximal end of the proximal member 14 to the distal end of the distal member 16. There, it may be secured to either distal end of the center support 20 or to the tip member 22. The stylet 24 is located within the catheter body 12 except in the area of the helical portion of the distal member 16. Here, apertures 26 and 28 are provided for ingress and egress. In order to insure that the stylet 24 moves smoothly through the catheter body 12, the stylet is located within a lubricated guide coil 30 (FIG. 2) in the preferred embodiment.

The exemplary catheter 10 illustrated in FIGS. 1–7 is not a steerable catheter and, accordingly, may be advanced though a conventional steerable guide sheath 32 to the target location. The sheath 32, which should be lubricious to reduce friction during movement of the catheter 10, may be advanced over a guidewire in conventional fashion. Alternatively, a steerable sheath may be provided. With respect to materials, the proximal portion of the sheath 14 is preferably a Pebax® and stainless steel braid composite and the distal portion is a more flexible material, such as unbraided Pebax®, for steering purposes. The sheath should also be stiffer than the catheter 12. Prior to advancing the catheter 10 into the sheath 32, the stylet 24 will be moved to and held in its distal most position (i.e. beyond the position illustrated in FIG. 3) in order to straighten out the helical portion of the distal member 16. The stylet 24 will remain in this position until the helical portion of the distal member 16 is advanced beyond the distal end of the sheath 32. A sheath introducer, such as those used in combination with basket catheters, may be used when introducing the distal member 16 into the sheath 32.

As illustrated for example in FIGS. 1, 3, 4 and 6, the exemplary catheter 10 may also include an anchor member 34 which allows the catheter to be precisely located relative to the pulmonary vein (or other orifice). More specifically, advancing the anchor member 34 into the pulmonary vein aligns the helical portion of the distal member 16 with the pulmonary vein. The physician can then manipulate the stylet 24 to bring the helical portion of the distal member 16 into the desired configuration and press the distal member (and electrodes 18) firmly against the region of tissue surrounding the pulmonary vein to create a circumferential lesion around the pulmonary vein. Alternatively, the physician can advance the helical portion of the distal member 16 into the pulmonary vein and thereafter manipulate the stylet 24 so that the helical portion expands and brings the electrodes 18 into contact with the interior of the pulmonary vein so that a circumferential lesion can be created within the vein. In the illustrated embodiment, the anchor member 34 is simply the portion of the distal member 16 that is distal to the helical portion. Alternatively, a separate structure may be secured to the distal end of the distal member 16. The exemplary anchor member 34 is approximately 1 to 2 inches in length, although other lengths may be used to suit particular applications.

Figure 11:
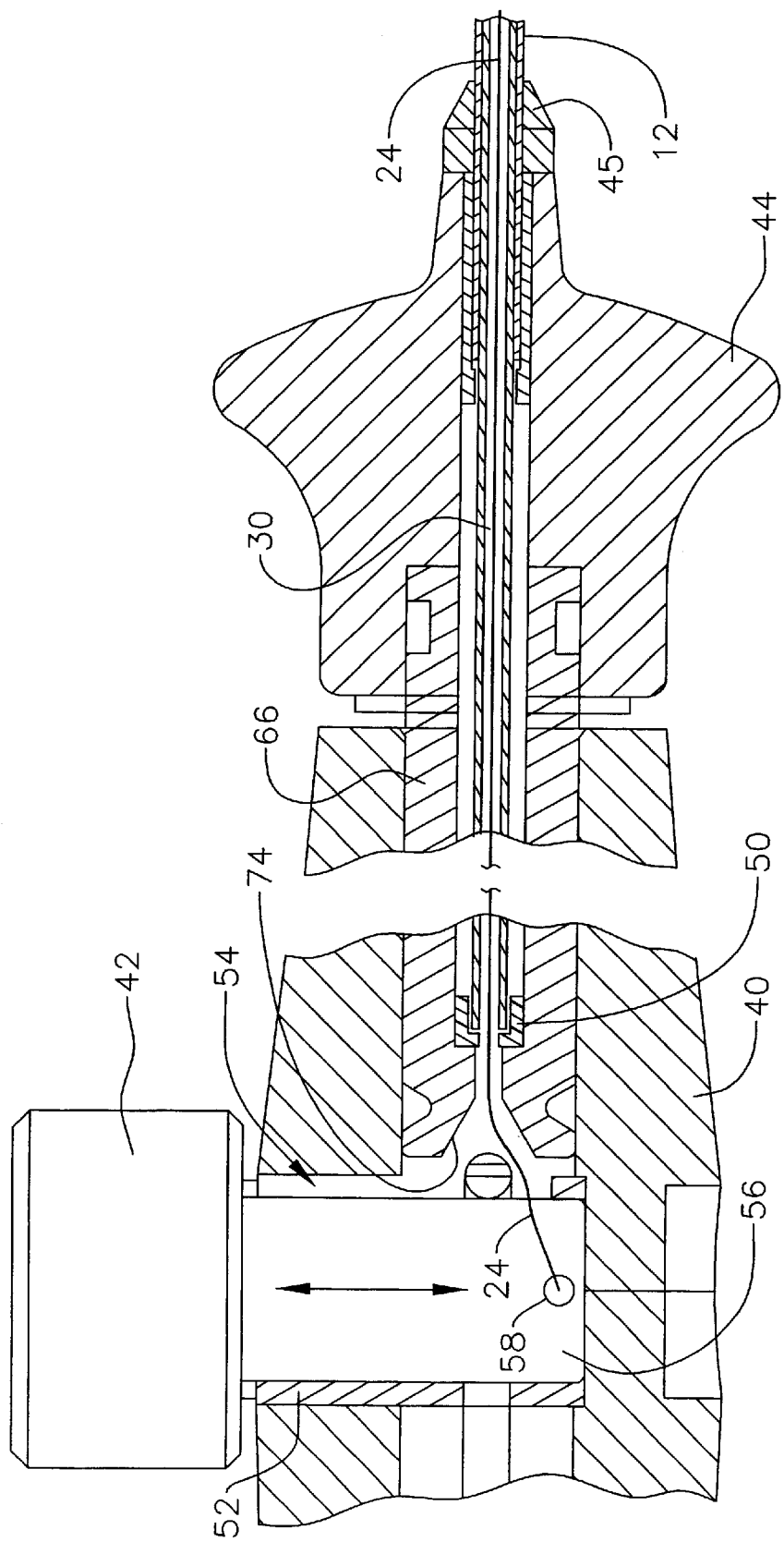
FIG. 11 is a partial section view taken along line 11—11 in FIG. 9.

The exemplary catheter 10 illustrated in FIGS. 1–7 should be used in conjunction with a handle that allows the physician to move the stylet 24 proximally and distally relative to the catheter body 12 and also allows the physician to rotate the stylet relative to the catheter body. One example of such a handle, which is generally represented by reference numeral 38, is illustrated in FIGS. 8–12. The handle 38 includes distal member 40, a rotatable knob 42 that is connected to the stylet 24 and a rotatable end cap 44 that is connected to the catheter body 12 through the use of a tip member 45. Specifically, the catheter body 12 is bonded to the tip member 45 which is in turn bonded to the rotatable end cap 44. The handle also includes a transition piece 46 that is used to secure the distal member 40 to a proximal member 48 (FIG. 11). The proximal end of the proximal member 48 includes a port (not shown) that receives an electrical connector from a power supply and control device. Alternatively, the distal and proximal members 40 and 48 may be combined into a unitary structure having a shape that is either the same as or is different than the illustrated shape of the combined distal and proximal members.

Turning first to the proximal and distal actuation of the stylet 24, the proximal portion of the stylet and lubricated guide coil 30 extend through the catheter body 12 and into the handle 38, as illustrated in FIG. 11. The lubricated guide coil 30 is secured to a seat 50 within the distal member 40. A stylet guide 52 that includes a guide slot 54 is secured within the distal member 40. The stylet guide 52 is preferably formed from a lubricious material such as acetal, which is sold under the trade name Delrin®. The stylet 24 passed through the guide slot 54 and is anchored to a threaded spool 56 that is secured to, and is preferably integral with, the rotatable knob 42. The rotatable knob and spool are secured to the proximal member 40 with a cap screw and nut arrangement or the like that extends through aperture 57 (FIG. 12). The threads on the spool 56 act as guides to control the manner in which the stylet 24 winds onto and unwinds from the spool. Anchoring is accomplished in the illustrated embodiment by inserting the stylet 24 into an anchoring aperture 58 and securing the stylet within the aperture with a set screw (not shown) that is inserted into a set screw aperture 60.

Proximal rotation of the knob 42 and threaded spool 56, i.e. rotation in the direction of arrow P in FIG. 9, will cause the stylet 24 to move proximally and wind onto the threaded spool. As this occurs, the stylet 24 will travel within the guide slot 54 towards the knob 42 in the direction of the arrow in FIG. 11. Distal rotation of the knob 42 on the other hand, i.e. rotation in the direction of arrow D in FIG. 9, will cause the stylet 24 to move distally, unwind from the threaded spool 56 and travel away from the knob within the guide slot 54.

In the preferred embodiment illustrated in FIGS. 8–12, the stylet 24 can be rotated relative to the catheter body 12 because the stylet is anchored with the handle distal member 40, while the catheter body is secured to the end cap 44 that is free to rotate relative to the distal member. Referring more specifically to FIGS. 10 and 11, the rotatable end cap 44 is mounted on an end cap support member 66. A set screw (not shown) engages a longitudinally extending slot 68 formed in the support member 66 and holds it in place within the distal member 40. The distal portion of the support member 66 includes a circumferentially extending slot 70. A series of set screws 72, which have a diameter that is substantially equal to the width of the slot 70, pass through the end cap 44 into the slot. This arrangement allows the end cap 44 to rotate relative to the support member 66 and, therefore, rotate relative to the handle distal member 40. The proximal end of the end cap support member 66 includes a relief surface 74 that prevents unnecessary stress on the stylet 24 as it travels back and forth within the guide slot 54.

To rotate the stylet 24 relative to the catheter body 12, the physician may hold the end cap 44 in place and rotate the handle distal member 40 relative to the end cap. When such rotation occurs, the stylet 24 will rotate within the catheter body 12. The catheter body 12, on the other hand, will be held in place by virtue of its connection to the end cap 40. As a result, the stylet 24 can be used to apply torsional forces to the helical portion of the proximal member 16 to move the helical portion between the various states illustrated in FIGS. 1, 4, and 6.

Figure 14:
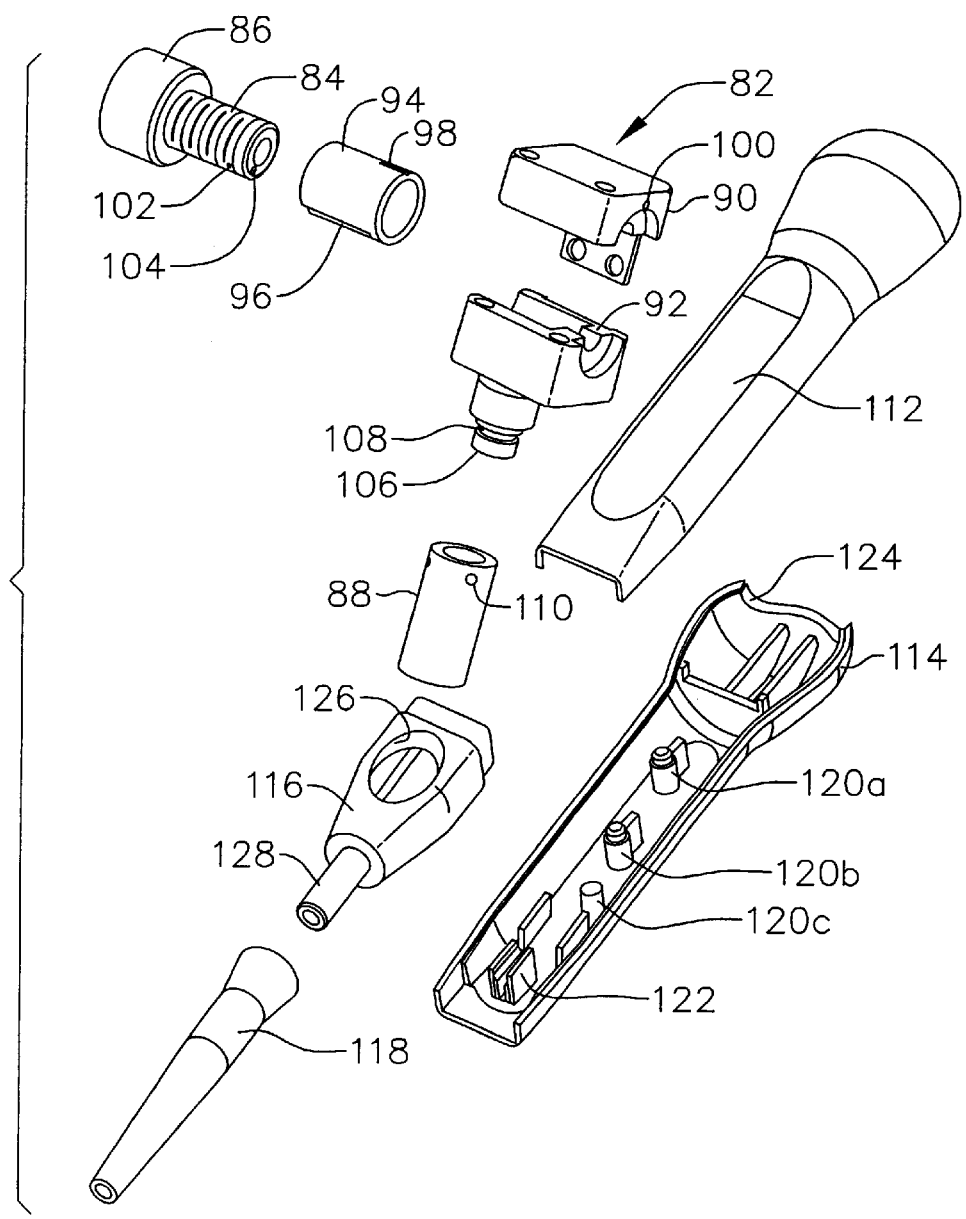
FIG. 14 is an exploded view of the probe handle illustrated in FIG. 13.

Another handle that may be used in conjunction with the exemplary catheter 10 is illustrated for example in FIGS. 13–15. Exemplary handle 76 includes a main body 78 and a stylet control device 80 that can be used to move the stylet 24 proximally and distally and that can also be used to rotate the stylet relative to the catheter body 12. The stylet control device 80 consists essentially of a housing 82, a rotatable threaded spool 84 and knob 86 arrangement, and a housing support member 88 that supports the housing such that the housing may be rotated relative to the main body 78.

The exemplary housing 82 is composed of two housing members 90 and 92 which fit together in the manner illustrated in FIG. 14. A stylet guide 94, which includes a guide slot 96, is located within the housing 82. The stylet guide 94 is secured in place and prevented from rotating relative to the housing 82 with a set screw (not shown) that rests within a positioning slot 98 after being inserted though an aperture 100 in the housing. The stylet 24 passes through the guide slot 96 and, in a manner similar to that described above with reference to FIGS. 8–12, is anchored in an anchoring aperture 102. The stylet 24 is secured within the anchoring aperture 102 with a set screw (not shown) that is inserted into a set screw aperture 104. Here too, proximal rotation of the knob 86 (arrow P in FIG. 13) will cause the stylet 24 to wind onto the threaded spool 84, thereby pulling the stylet proximally, while distal rotation (arrow D in FIG. 13) will cause the stylet to unwind from the spool and move distally.

In the preferred embodiment illustrated in FIGS. 13–15, the housing 82 includes a post 106 that may be inserted into the housing support member 88, which is itself fixedly secured to the handle main body 78. A circumferentially extending slot 108 is formed in one end of the post 106. In a manner similar to the end cap 44 illustrated in FIGS. 8–12, the post 106 may be secured to the housing support member 88 by inserting a series of set screws 110 though a corresponding series of support member apertures and into the slot 108. As described in greater detail below with reference to FIG. 15, the catheter body 12 is fixedly secured to the handle main body 78. Thus, rotation of the housing 82 relative to the housing support member 88 and, therefore, the main body 78 will cause the stylet 24 to rotate relative to the catheter body 12. Upon such rotation, the stylet 24 will apply torsional forces to the helical portion of the proximal member 16, thereby causing it to move between the states illustrated in FIGS. 1, 4, and 6.

As illustrated for example in FIG. 14, the exemplary handle main body 78 is a multi-part assembly consisting of handle members 112 and 114, a base member 116 and a strain relief element 118. Handle member 114 includes a series of fasteners 120a–c which mate with corresponding fasteners (not shown) on the handle member 112. Handle member 114 also includes a wire guide 122 which is used to centralize the electrical wires. A cutout 124 is formed at the proximal end of the handle member 114 and a similar cutout (not shown) is formed in the handle member 112. The cutouts together form an opening for an electrical connector from a power supply and control device. The base member 116 includes an aperture 126 for seating the housing support member 88 and a cylindrical post 128 on which the strain relief element 118 is fixedly mounted.

The catheter body 12 may be inserted into and bonded to the base member 116 in the manner illustrated for example in FIG. 15. Thus, the catheter body 12 is fixed relative to the handle 76. The guide coil 30 is secured within a guide coil seat 130 and the stylet 24 extends through the guide coil seat and into the housing support member 88 in the manner shown.

Figure 16:
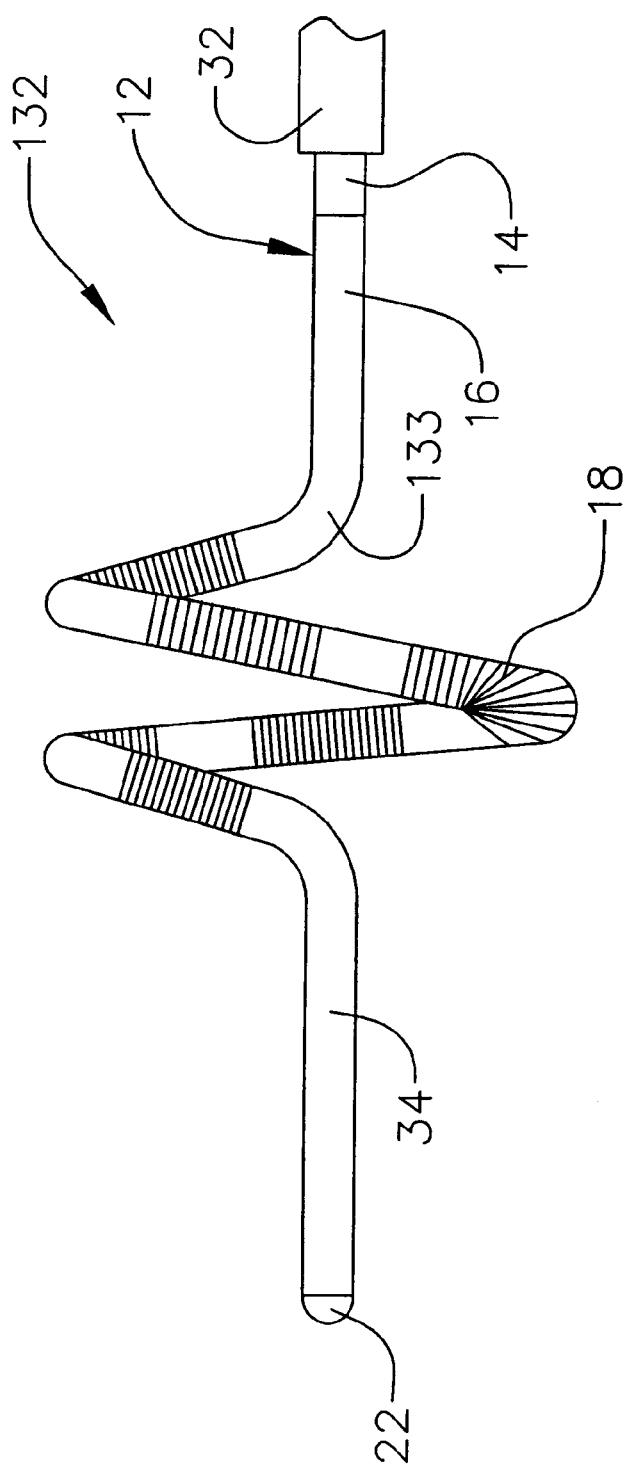
FIG. 16 is a side view of a probe in accordance with a preferred embodiment of a present invention.

Like the catheter illustrated in FIGS. 1–7, the helical catheter 132 illustrated in FIG. 16 includes a catheter body 12 having a proximal member 14 and a distal member 16 with a helical portion, a plurality of electrodes 18, and an anchor member 34. The catheter illustrated in FIG. 16 does not, however, include a stylet 24. Here too, the center support may be formed from resilient inert wire, such as Nickel Titanium (commercially available under the trade name Nitinol®) or 17-7 stainless steel wire, with a portion thereof heat set into the desired helical configuration. In order to compensate for the decrease in manipulability associated with the lack of a stylet, the center support may, alternatively, be formed from material such as actuator-type Nitinol® (discussed in detail below) which has shape memory properties that are activated at a temperature higher than body temperature. The shape memory properties allow the physician to, for example, cause the helical portion of the distal member 16 to expand from the state illustrated in FIGS. 4–5b (albeit with respect to catheter 10) to the state illustrated in FIGS. 6 and 7 by energizing the electrodes 18. Also, because the catheter 132 lacks the stylet 24, it may be used in conjunction with any conventional catheter handle.

The helical portion of the distal member 16 in the catheter 132 should be flexible enough that the helical portion will deflect and straighten out when pushed or pulled into the sheath, yet resilient enough that it will return to its helical shape when removed from the sheath. In addition, the proximal and distal end of the helical portion should be oriented at an angle relative to the longitudinal axis of the catheter 36 (preferably between about 30 and about 60 degrees and most preferably about 45 degrees) that facilitates a smooth transition as the distal member 16 is pushed or pulled into the sheath 32. To that end, the exemplary distal member 16 (and internal center support) includes a pre-bent curved portion 133.

The pre-bent curved portion 133 will typically be bent out of its pre-bent orientation when the catheter body 12 and helical portion are urged against tissue. The internal center support will then generate a spring force that also urges the helical portion against the tissue and improves tissue/electrode contact. Additionally, because the curved portion 133 is located along the axis of the helical structure, the spring force will be distributed evenly around the circumference of the helical portion.

Figure 16A:
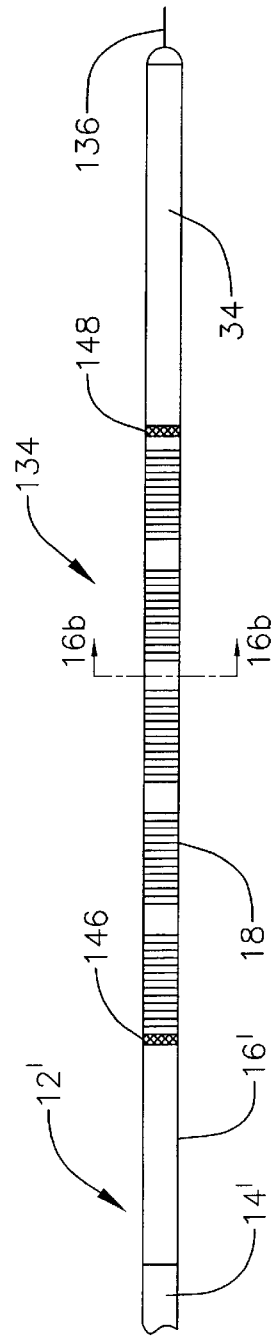
FIG. 16a is a side view of a probe in accordance with a preferred embodiment of a present invention.
Figure 16C:
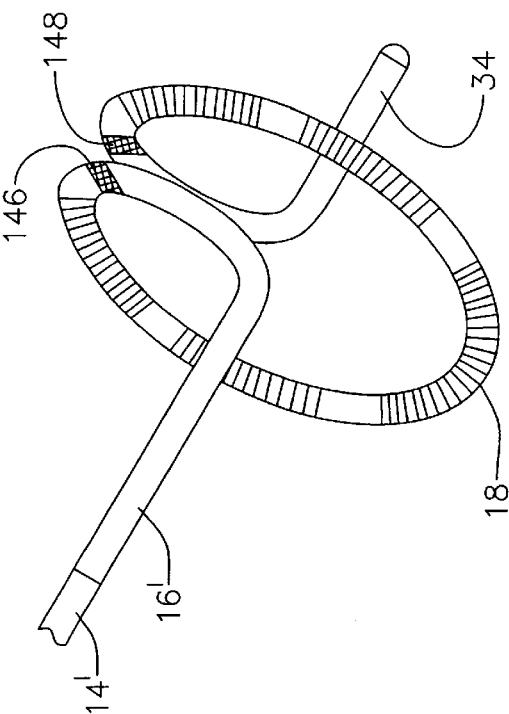
FIG. 16c is a perspective view of the probe illustrated in FIG. 16a in a helical orientation.
Figure 16B:
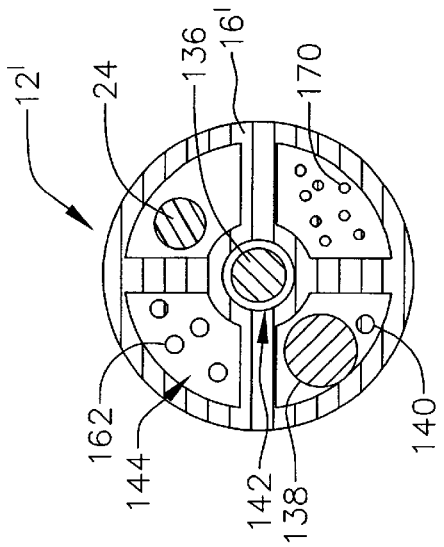

Another exemplary catheter that relies on materials which have shape memory properties activated at high temperatures is illustrated in FIGS. 16a–16c. Exemplary catheter 134, which is a non-steerable catheter that may be inserted into a patient over a guidewire 136, includes a catheter body 12' having a proximal member 14' and a distal member 16', a plurality of electrodes 18, and an anchor member 34. The catheter 134 also includes a shape memory core wire 138 that is friction fit within the distal member 16' and heat set into a helical configuration. The core wire 138 is relatively flexible at body temperature. As such, a stylet 24 may be used to maintain the core wire 138 and electrode supporting distal member 16' in the linear state illustrated in FIG. 16a.

The core wire 138 and distal member 16' may be driven to the helical state illustrated in FIG. 16c by heating the core wire 138. Resistive heating is the preferred method of heating the core wire 138. To that end, electrical leads 140 (only one shown) are connected to the ends of the core wire 138 and supply current to the core wire. The stylet 24 and guidewire 136 should be pulled in the proximal direction beyond the distal member 16' prior to heating the core wire 138.

A suitable material for the core wire 138 is a shape memory alloy such as actuator-type Nitinol®. Such material has a transition temperature above body temperature (typically between about 55° C. and 70° C.). When the material is heated to the transition temperature, the internal structure of the material dynamically changes, thereby causing the material to contract and assume its heat set shape. Additional information concerning shape memory alloys is provided in T. W. Duerig et al., "Actuator and Work Production Devices," *Engineering Aspects of Shape Memory Alloys*, pp. 181–194 (1990).

The exemplary catheter body 12' is substantially similar to the catheter body 12 described above. However, as illustrated in FIG. 16b, the exemplary catheter body 12' includes five lumens—a central lumen 142 and four outer lumens 144. The guidewire 136 passes through the central lumen 142. The core wire 138 and conductor 140 are located within one of the outer lumens 144 and the stylet 24 is located in another outer lumen. The other two outer lumens 144 respectively house electrode wires 162 and temperature sensor wires 170 (discussed in Section IV below). Of course, other catheter body configurations, such as a three outer lumen configuration in which the electrode and temperature sensor wires are located in the same lumen, may be employed.

The exemplary catheter 134 illustrated in FIGS. 16a–16c also includes a pair of radiopaque markers 146 and 148 that may be used to properly position the helical portion of the catheter. More specifically, because the core wire 138 contracts equally in the distal and proximal directions, the catheter 134 should be positioned such that the target tissue area is located at about the mid-point between the radiopaque markers 146 and 148 prior to actuating the core wire 138. To form a lesion within the pulmonary vein, for example, the anchor member 34 may be inserted into the pulmonary vein to such an extent that the mid-point between the radiopaque markers 146 and 148 is located at the target site within the vein. Actuation of the core wire 138 will cause the electrode supporting distal member 16' to assume the helical shape illustrated in FIG. 16c and press against the vein so as to achieve a suitable level of tissue contact.

Once the lesion has been formed, the core wire 138 may be deactivated and the stylet 24 may be moved back into the distal member 16' to return the distal member to the linear state illustrated in FIG. 16a. A diagnostic catheter (not shown) may then be advanced through the central lumen 142 to map the vein and insure that a curative lesion has been formed.

Another exemplary helical catheter, which is generally represented by reference numeral 150 in FIGS. 17–20, includes a catheter body 12 having a proximal member 14 and a distal member 16 with a helical portion, a plurality of electrodes 18, and an anchor member 34. The helical catheter 150 illustrated in FIGS. 17–20 is similar to the helical catheter 132 illustrated in FIG. 16 in that the catheter 150 includes a pre-bent curved portion 151 and lacks a stylet 24. [A stylet 24 may nevertheless be added, as is described below with reference to FIG. 23.] The helical catheter 150 illustrated in FIGS. 17–20 differs from the catheter 132 illustrated in FIG. 16 in that (1) the helical portion of the catheter 150 tapers from a larger proximal diameter down to a smaller distal diameter and/or (2) steps are taken to increase the flexibility of the distal portion of the distal member 16. Preferably, the distal portion of the distal member 16 in the helical catheter 150 will be more flexible than the proximal portion of the distal member. Each of these features provides unique benefits.

Turning first to the taper of the helical portion in the exemplary helical catheter 150, an embodiment configured for use with the pulmonary veins will preferably have a proximal coil outer diameter that will cause the proximal portion to abut the pulmonary vein ostium (i.e. between about 15 mm and about 35 mm) and a distal coil outer diameter suitable for placement within the pulmonary vein (i.e. between about 5 mm and about 10 mm). The helical catheter 150 will, therefore, be self-centering when inserted into the pulmonary vein in the manner illustrated in FIG. 19 because the tapered helical portion will wedge itself against the pulmonary vein ostium and the internal wall of pulmonary vein itself. Not only does this result in proper positioning of the electrodes 18, the wedging effect also prevents beating related movement of the heart from the knocking the helical catheter 150 out of position once it is in place.

With respect to variations in flexibility, it should first be noted that a tapered helical structure having uniform construction (and uniform stiffness when uncoiled) will become stiffer as the diameter of the helical coils decreases. Absent the inventions disclosed herein, a catheter with a tapered helical region having uniform construction would become stiffer as the diameter of the helical coils decreases and the stiffest portion of the catheter's helical region would be the distal portion which, as discussed below, is undesirable. The inventions disclosed herein will, at a minimum, reduce the amount of the increase in stiffness at the smaller diameter distal coils and, preferably, will reduce the stiffness to a level that is less than the stiffness of the larger diameter proximal coils. The stiffness of the helical region may, for example, decrease at a non-zero rate from the proximal end to the distal end. This may be accomplished by making the catheter construction non-uniform and reducing the stiffness of portions of the catheter, measured when the catheter is uncoiled, which results in a corresponding reduction in stiffness when coiled. It also should be noted here that the coil stiffness and flexibility referred to herein are coaxial stiffness, i.e. stiffness in the compression direction along the longitudinal axis of the helical portion of the catheter.

Referring to FIGS. 17 and 19, the distal member 16 of the exemplary helical catheter 150 includes a distal portion 152 that is relatively flexible and a proximal portion 154 that is relatively stiff. As a result, there is a non-linear force distribution through the coils.

The differences in stiffness allow the present catheter to accomplish a number of normally competing goals. One goal is preventing tissue damage. Typically, the physician will poke around within the atrium as attempts are made to insert the helical structure into a pulmonary vein. The more flexible distal portion 152 will, of course, be less likely to traumatize tissue during this process. It is also important that the helical portion be predisposed to easily uncoil for placement within the sheath 32, remain uncoiled and slide though the sheath until it exits through the distal end of the sheath and re-coils, and then easily uncoil again when pulled back into the sheath after the procedure is completed. The stiffer the coils are, the more likely they are to resist uncoiling, which makes it more difficult to get the helical structure into the sheath, and to re-coil within the sheath, which creates friction and makes it more difficult to slide the helical structure through the sheath. Thus, the more flexible distal portion 152 will also improve these aspects of the procedure. Achieving good tissue/electrode contact is a primary goal in any lesion creation procedure. The stiffer proximal portion 154 allows the physician to press the electrodes 18 against the tissue with more force when lesions are being created.

Figure 20:
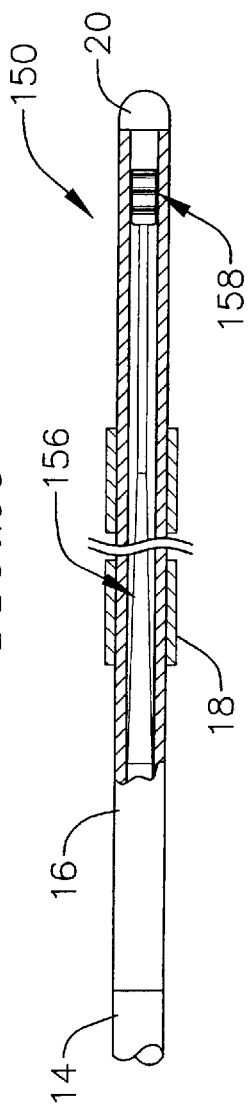
FIG. 20 is side, partial section view of the distal portion of the probe illustrated in FIG. 17 in a straightened orientation.

Increasing the flexibility of the distal portion 152 may be accomplished in a variety of ways. As illustrated for example in FIGS. 20–22, the exemplary helical catheter 150 includes a core wire 156 that has three sections—a full cross-sectional area section 156a, a tapered section 156b and a reduced cross-sectional area section 156c. [Cross-sectional area is measured in a plane that is perpendicular to the centerline CL.] The core wire 156 extends the length of the catheter. The proximal end of the core wire 156 is secured to the catheter handle (not shown), while the distal end is secured to a crimp tube 158 that is soldered to the tip 22 (FIG. 20).

The exemplary core wire 156 is preferably formed from resilient inert wire, such as Nitinol® Nickel Titanium or 17-7 stainless steel wire, heat set into the desired helical configuration. Alternatively, material such as the aforementioned actuator-type Nitinol® which has shape memory properties that are activated at a temperature higher than body temperature may be employed.

Figure 21:
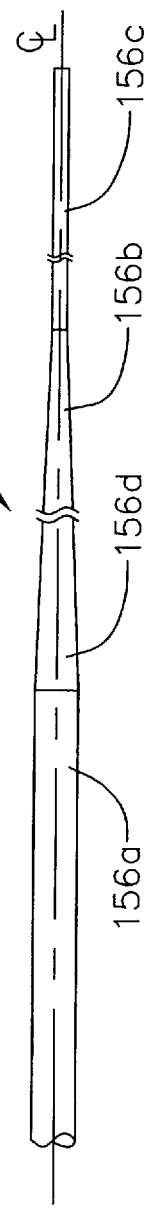
FIG. 21 is a side view of a core wire in accordance with a preferred embodiment of a present invention in a straightened orientation.
Figure 22:
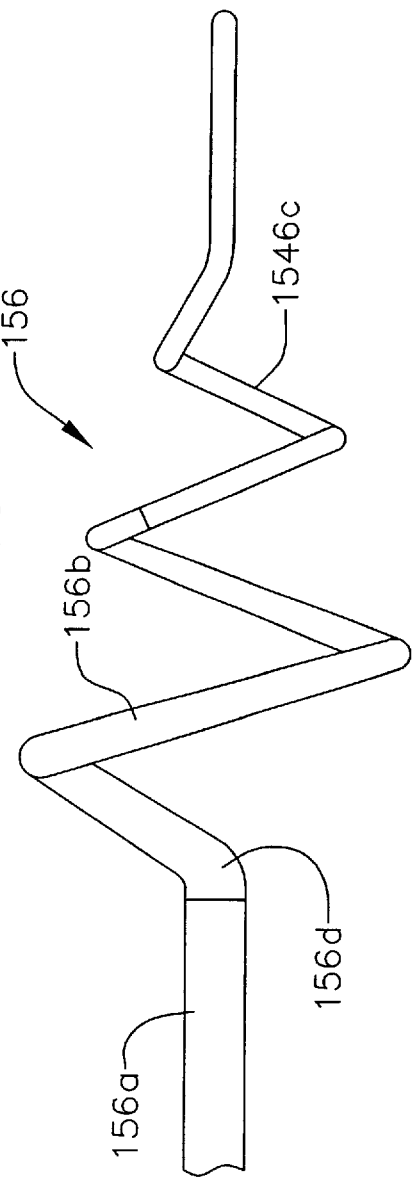
FIG. 22 is a side view of the core wire illustrated in FIG. 21 in a coiled orientation.

Although other shapes and sizes may be employed, the core wire 156 is preferably cylindrical in shape and has the following dimensions: the diameter of section 156a is about 0.022 inch, the diameter of section 156c is about 0.012 inch and, when in the straightened state illustrated in FIG. 21, section 156b is about 4.25 inches in length and section 156c is about 3.00 inches in length. When in the coiled state illustrated in FIG. 22, the coiled region including section 156b and a portion of section 156c is about 1.25 inches in length and the remaining linear portion of section 156c (which is within the anchor member 34) is about 0.75 inch in length. Such a core wire will necessarily result in a distal portion 152 that is less stiff than it would have been if the entire core wire had the diameter of section 156a. In order to insure that the distal portion 152 is in fact less stiff than the proximal portion 154, section 156c may be reduced in diameter and/or increased in length thereby causing section 156b to taper down to a smaller diameter and/or have a shorter length.

Other methods of increasing the flexibility of the distal portion 152 include forming the distal member 16 from variable stiffness tubing. For example, the tubing may have two portions, i.e. a higher durometer proximal portion and a lower durometer distal portion secured to one another, or may be unitary and simply vary in stiffness continuously over its length from a higher durometer at the proximal end to a lower durometer at the distal end. The tubing used to form the distal member 16 may also be tapered such that the diameter of the tubing decreases from a larger diameter at the proximal end to a smaller diameter at the distal end. Here too, this may be accomplished by employing a two portion design, i.e. two portions having different, but constant diameters secured to one another, or a unitary design where the diameter drops continuously over the length of the tubing.

The exemplary core wire 156 also includes a pre-bent curved area 156d that creates the catheter's pre-bent curved portion 151. In the illustrated embodiment, the curved area 156d orients the proximal region of section 156b at an angle between about 30 and about 60 degrees, and preferably about 45 degrees, relative to the longitudinal axis of the catheter. The pre-bent curved portion 151 and curved area 156d will be bent out of their pre-bent orientation (shown in dashed lines) when the catheter body 12 is urged distally in the direction of arrow A (as shown in dashed lines). The bending of the core wire curved area 156d will then generate a spring force that urges the helical portion against the tissue and improves tissue/electrode contact over and above that which would be obtained by simply urging the helical portion distally against the tissue. Additionally, because the curved portion 151 is located along the axis of the helical portion, the spring force will be distributed evenly around the circumference of the helical portion.

Figure 23:
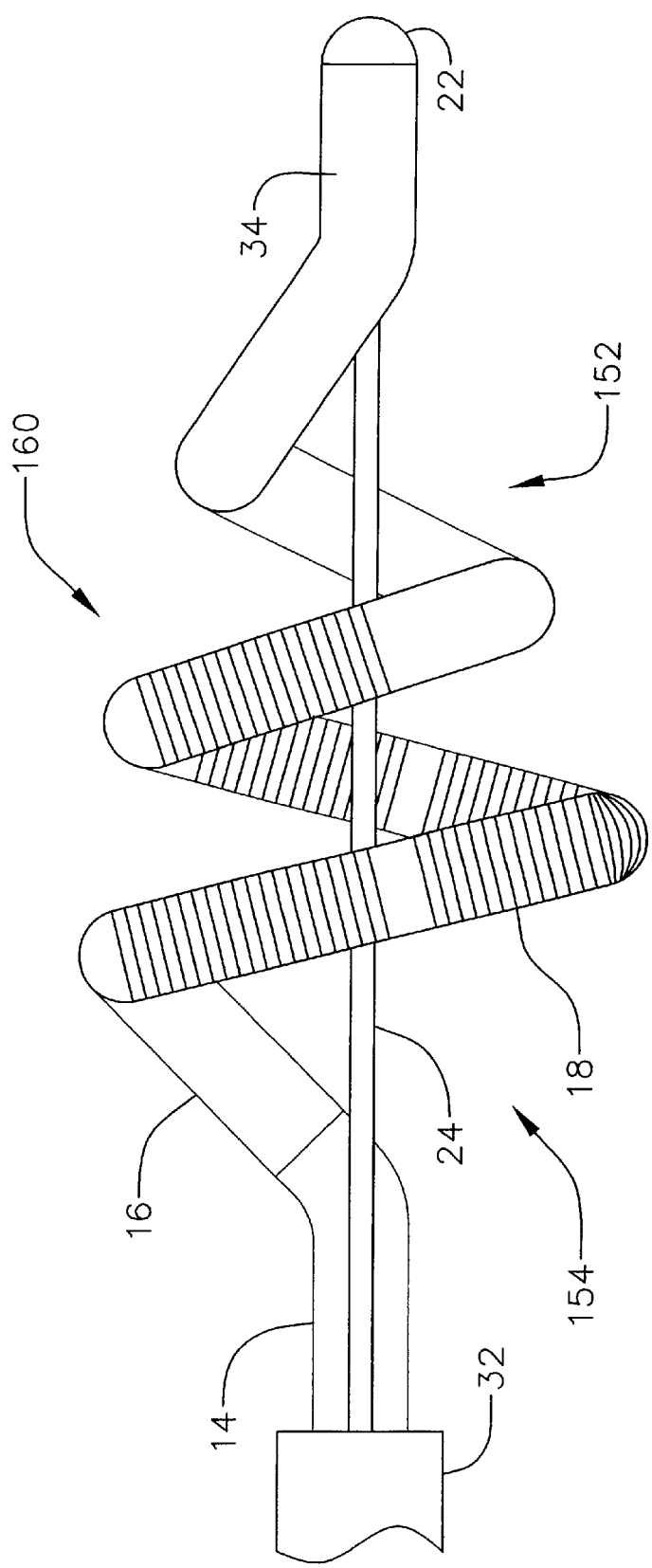
FIG. 23 is a side view of a probe in accordance with a preferred embodiment of a present invention.

As illustrated for example in FIG. 23, a helical catheter 160 in accordance with one embodiment of a present invention is essentially identical to the catheter 150 illustrated in FIGS. 17–22, except the it includes a stylet 24. The stylet 24 is secured within the anchor member 34 in the manner described above with reference to FIG. 1. [Note that aperture 26 is not visible in FIG. 23.] Here, however, because the larger diameter portion of the core wire 156 (i.e. section 156a) occupies most of the interior of catheter body proximal member 14, the stylet 24 does not re-enter the catheter body proximal to the helical portion. Instead, the stylet merely runs through the sheath 32 along the exterior of the proximal member 14. The proximal end of the stylet may be either left free, so that it can be directly manipulated by the physician, or secured to a manipulation device on a catheter handle such as, for example, one of the handles described above with reference to FIGS. 8–15.

III. Pre-Oriented Loop Structures

An exemplary catheter 161 in accordance with a present invention is illustrated in FIGS. 24–26. The catheter 161 is similar to the helical catheters illustrated in FIGS. 1–7 and 16–23 in that it includes a catheter body 12 having a proximal and distal members 14 and 16 formed from the materials described above and is advanced through a sheath 32. Here, however, the catheter 161 includes a pre-set curved portion (or elbow) 163 and a pull wire 165 which extends from the distal end of the catheter and back through the sheath 32. The pull wire 165 is used to pull the distal member 16 into a loop configuration. The pull wire 165 also maintains the shape of the loop (thereby insuring good tissue contact) when the loop is urged against tissue, such as a pulmonary vein ostium. More specifically, tension on the pull wire 165 prevents the distal end of the catheter, which is adjacent the distal end of the sheath 32 in the loop orientation, from being pushed proximally relative to the distal end of the sheath when the catheter 161 is urged distally against tissue.

Referring first to the pre-set curved portion 163, the curved portion in the illustrated embodiment is has a 90 degree curve in the horizontal (as shown) catheter plane (if flattened within the catheter plane) with a radius of about 0.5 inch and a curve of between about 30 and about 60 degrees, and preferably about 45 degrees, out of the horizontal catheter plane which orients the catheter in the manner illustrated in FIGS. 24 and 25. As a result, the loop plane is offset between about 30 and about 60 degrees from the catheter plane. The preset curvature may be accomplished in a variety of ways. Preferably, the curved portion 163 is preset through the use of a thermal forming technique (100° C. for 1 hour). The preset curvature may also be accomplished through the use of a pre-shaped core wire 171 (FIG. 25) formed from Nitinol® or 17-7 stainless steel. The curved portion 163 will typically be bent out of its pre-bent orientation when the loop is urged against tissue (note the dashed lines in FIG. 25). As a result, the curved portion 163 will generate a spring force that urges the loop against the tissue and improves tissue/electrode contact.

The pull wire 165 is preferably a flexible, inert cable constructed from strands of metal wire material, such as Nitinol® or 17-7 stainless steel, that is about 0.012 inch to about 0.025 inch in diameter. Alternatively, the pull wire 165 may be formed from a flexible, inert stranded or molded plastic material. The pull wire 165 is also preferably round in cross-section, although other cross-sectional configurations can be used.

As illustrated for example in FIG. 26, the pull wire 165 in the exemplary embodiment extends into an opening 167 in a tip member 169 and is secured to the core wire 171 with a stainless steel crimp tube 173. More specifically, the pull wire 165 passes through a bore 175 in the distal end 177 of the crimp tube 173 and abuts the core wire 171. The tip member 169 is preferably formed from platinum and is fixedly engaged with, for example, silver solder, adhesive or spot welding, to the distal end 177 of crimp tube 173. The center support may be electrically insulated with a thin walled polyester heat shrink tube 179 that extends beyond the proximal end of the crimp tube 173.

The pull wire 165 extends proximally from the tip member 169 and runs proximally within the interior of the sheath 32 along the exterior of the catheter body 12. Alternatively, the pull wire can extend back into the catheter body 12 through an aperture (not shown) near the pre-set portion 163 to the end of the catheter body. The proximal end of the pull wire 165 may be held in place by hand or secured to a handle in order to maintain tension on the pull wire. Other pull wire configurations, other methods of attaching the pull wire to the catheter body, and methods of reducing stress on the pull wire are disclosed in U.S. Pat. No. 6,048,329.

IV. Electrodes, Temperature Sensing and Power Control

In each of the preferred embodiments, the operative elements are a plurality of spaced electrodes 18. However, other operative elements, such as lumens for chemical ablation, laser arrays, ultrasonic transducers, microwave electrodes, and ohmically heated hot wires, and such devices may be substituted for the electrodes. Additionally, although electrodes and temperature sensors are discussed below in the context of the exemplary catheter probe illustrated in FIGS. 1–7, the discussion is applicable to all of the probes disclosed herein.

The spaced electrodes 18 are preferably in the form of wound, spiral coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred coil electrode is disclosed in U.S. Pat. No. 5,797,905. The electrodes 18 are electrically coupled to individual wires 162 (see, for example, FIG. 2) to conduct coagulating energy to them. The wires are passed in conventional fashion through a lumen extending through the associated catheter body into a PC board in the catheter handle, where they are electrically coupled to a connector that is received in a port on the handle. The connector plugs into a source of RF coagulation energy.

As an alternative, the electrodes may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The flexible electrodes 18 are preferably about 4 mm to about 20 mm in length. In the preferred embodiment, the electrodes are 12.5 mm in length with 1 mm to 3 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

The portion of the electrodes that are not intended to contact tissue (and be exposed to the blood pool) may be masked through a variety of techniques with a material that is preferably electrically and thermally insulating. This prevents the transmission of coagulation energy directly into the blood pool and directs the energy directly toward and into the tissue. For example, a layer of UV adhesive (or another adhesive) may be painted on preselected portions of the electrodes to insulate the portions of the electrodes not intended to contact tissue. Deposition techniques may also be implemented to position a conductive surface only on those portions of the assembly intended to contact tissue. Alternatively, a coating may be formed by dipping the electrodes in PTFE material.

The electrodes may be operated in a uni-polar mode, in which the soft tissue coagulation energy emitted by the electrodes is returned through an indifferent patch electrode (not shown) externally attached to the skin of the patient. Alternatively, the electrodes may be operated in a bi-polar mode, in which energy emitted by one or more electrodes is returned through other electrodes. The amount of power required to coagulate tissue ranges from 5 to 150 w.

Figure 5A:
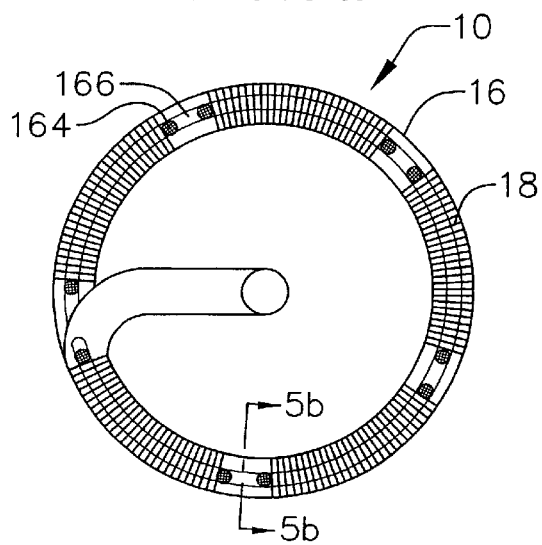
FIG. 5a is an end view of the probe illustrated in FIG. 4.
Figure 5B:
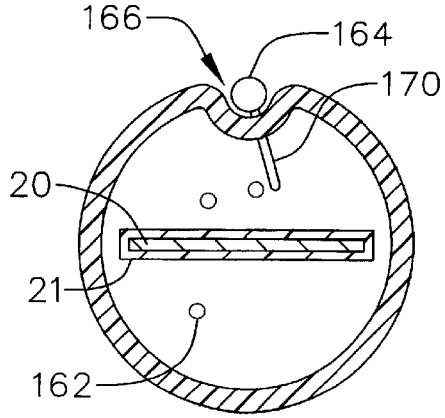
Figure 6:
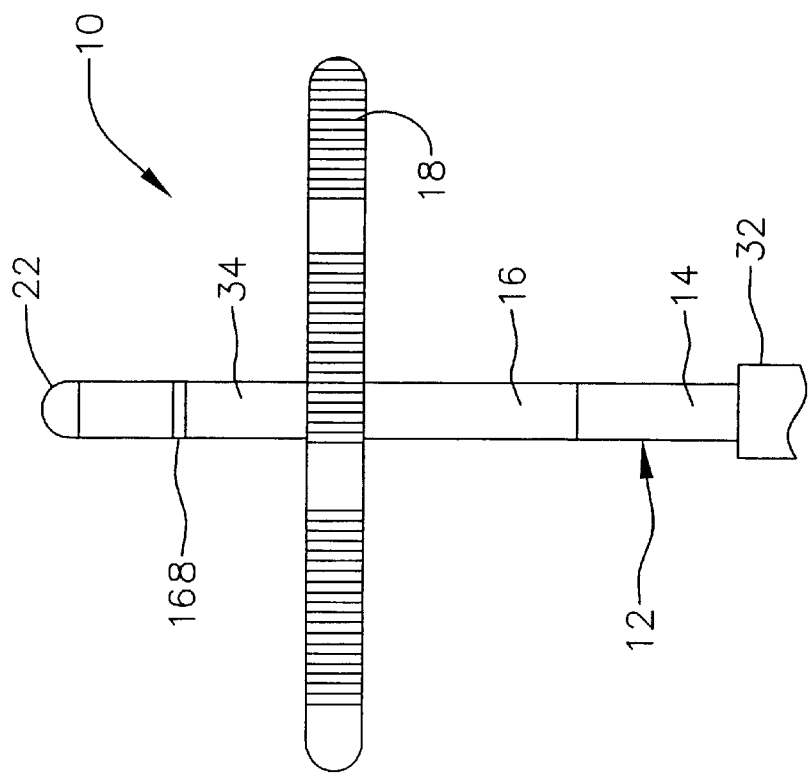
FIG. 6 is a side view of the probe illustrated in FIG. 1 in an expanded state.

As illustrated for example in FIGS. 5*a* and 5*b*, a plurality of temperature sensors 164, such as thermocouples or thermistors, may be located on, under, abutting the longitudinal end edges of, or in between, the electrodes 18. Preferably, the temperature sensors 164 are located at the longitudinal edges of the electrodes 18 on the distally facing side of the helical (or other loop) structure. In some embodiments, a reference thermocouple 168 may also be provided. For temperature control purposes, signals from the temperature sensors are transmitted to the source of coagulation energy by way of wires 170 (FIG. 2) that are also connected to the aforementioned PC board in the catheter handle. Suitable temperature sensors and controllers which control power to electrodes based on a sensed temperature are disclosed in U.S. Pat. Nos. 5,456,682, 5,582,609 and 5,755,715.

The temperature sensors 164 are preferably located within a linear channel 166 that is formed in the distal member 16. The linear channel 166 insures that the temperature sensors will directly face the tissue and be arranged in linear fashion. The illustrated arrangement results in more accurate temperature readings which, in turn, results in better temperature control. As such, the actual tissue temperature will more accurately correspond to the temperature set by the physician on the power control device, thereby providing the physician with better control of the lesion creation process and reducing the likelihood that embolic materials will be formed. Such a channel may be employed in conjunction with any of the electrode (or other operative element) supporting structures disclosed herein.

Finally, the electrodes 18 and temperature sensors 168 can include a porous material coating, which transmits coagulation energy through an electrified ionic medium. For example, as disclosed in U.S. Pat. No. 5,991,650, electrodes and temperature sensors may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

Although the present inventions have been described in terms of the preferred embodiments above, numerous modifications and/or additions to the above-described preferred embodiments would be readily apparent to one skilled in the art. By way of example, but not limitation, the anchor member 34 may be eliminated from any of the illustrated embodiments. Moreover, the inventions includes any and all combinations of the elements from the various embodiments disclosed in the specification. It is intended that the scope of the present inventions extend to all such modifications and/or additions and that the scope of the present inventions is limited solely by the claims set forth below.

I claim:

1. A probe, comprising:
   a probe body defining a distal region, a proximal region and a longitudinal axis;
   a helical structure associated with the distal region of the probe body and movable between a coiled and uncoiled configuration, the helical structure defining proximal and distal ends, proximal and distal end diameters, and proximal and distal end stiffnesses, the distal end diameter being less than the proximal end diameter when in the coiled configuration and the distal end stiffness being less than the proximal end stiffness at least when in the uncoiled configuration; and
   at least one tissue coagulation element supported on the helical structure.

2. A probe as claimed in claim 1, wherein the probe body comprises a catheter body.

3. A probe as claimed in claim 1, wherein the helical structure defines a longitudinal axis coincident with the longitudinal axis of the probe body.

4. A probe as claimed in claim 1, wherein the helical structure defines a longitudinal axis and completes at least one revolution about the longitudinal axis.

5. A probe as claimed in claim 1, wherein the helical structure defines a longitudinal axis and completes at least two revolutions about the longitudinal axis.

6. A probe as claimed in claim 1, wherein the stiffness of the helical structure decreases at a non-zero rate from the proximal end to the distal end.

7. A probe as claimed in claim 1, wherein the helical structure includes a core wire defining a core wire stiffness at the proximal end of the helical structure and a core wire stiffness at the distal end of the helical structure that is less than the core wire stiffness at the proximal end of the helical structure.

8. A probe as claimed in claim 7, wherein the core wire defines a cross-sectional area at the proximal end of the helical structure and a cross-sectional at the distal end of the helical structure that is less than the cross-sectional area at the proximal end of the helical structure.

9. A probe as claimed in claim 8, wherein the core wire defines a substantially constant taper over at least a portion thereof.

10. A probe as claimed in claim 7, wherein the core wire comprises shape memory material.

11. A probe as claimed in claim 10, wherein the shape memory material is activated at temperatures above body temperature.

12. A probe as claimed in claim 1, wherein the at least one tissue coagulation element comprises a plurality of electrodes.

13. A probe as claimed in claim 1, further comprising:
an anchor member associated with the distal end of the helical structure and extending distally therefrom.

14. A probe as claimed in claim 1, further comprising:
a control element associated with the helical structure and extending to the proximal region of the probe body.

15. A probe, comprising:
a probe body defining a distal region, a proximal region and a longitudinal axis;
a helical structure associated with the distal region of the probe body and defining proximal and distal ends;
a core wire located within the helical structure and defining a core wire stiffness at the proximal end of the helical structure and a core wire stiffness at the distal end of the helical structure that is less than the core wire stiffness at the proximal end of the helical structure; and
at least one tissue coagulation element supported on the helical structure.

16. A probe as claimed in claim 15, wherein the probe body comprises a catheter body.

17. A probe as claimed in claim 15, wherein the helical structure defines a longitudinal axis coincident with the longitudinal axis of the probe body.

18. A probe as claimed in claim 15, wherein the helical structure defines a longitudinal axis and completes at least one revolution about the longitudinal axis.

19. A probe as claimed in claim 15, wherein the helical structure defines a longitudinal axis and completes at least two revolutions about the longitudinal axis.

20. A probe as claimed in claim 15, wherein the core wire defines a cross-sectional area at the proximal end of the helical structure and a cross-sectional at the distal end of the helical structure that is less than the cross-sectional area at the proximal end of the helical structure.

21. A probe as claimed in claim 20, wherein the core wire defines a substantially constant taper over at least a portion thereof.

22. A probe as claimed in claim 20, wherein the core wire comprises shape memory material.

23. A probe as claimed in claim 22, wherein the shape memory material is activated at temperatures above body temperature.

24. A probe as claimed in claim 15, wherein the at least one tissue coagulation element comprises a plurality of electrodes.

25. A probe as claimed in claim 15, further comprising:
an anchor member associated with the distal end of the helical structure and extending distally therefrom.

26. A probe as claimed in claim 15, further comprising:
a control element associated with the helical structure and extending to the proximal region of the probe body.

27. A probe, comprising:
a probe body defining a distal region, a proximal region and a longitudinal axis;
a helical structure associated with the distal region of the probe body and defining proximal and distal ends;
a core wire located within the helical structure and defining a cross-sectional area at the proximal end of the helical structure and a cross-sectional area at the distal end of the helical structure that is less than the cross-sectional area at the proximal end of the helical structure; and
at least one tissue coagulation element supported on the helical structure.

28. A probe as claimed in claim 27, wherein the probe body comprises a catheter body.

29. A probe as claimed in claim 27, wherein the helical structure defines a longitudinal axis coincident with the longitudinal axis of the probe body.

30. A probe as claimed in claim 27, wherein the helical structure defines a longitudinal axis and completes at least one revolution about the longitudinal axis.

31. A probe as claimed in claim 27, wherein the helical structure defines a longitudinal axis and completes at least two revolutions about the longitudinal axis.

32. A probe as claimed in claim 27, wherein the core wire defines a substantially constant taper over at least a portion thereof.

33. A probe as claimed in claim 27, wherein the core wire comprises shape memory material.

34. A probe as claimed in claim 33, wherein the shape memory material is activated at temperatures above body temperature.

35. A probe as claimed in claim 27, wherein the at least one tissue coagulation element comprises a plurality of electrodes.

36. A probe as claimed in claim 27, further comprising:
an anchor member associated with the distal end of the helical structure and extending distally therefrom.

37. A probe as claimed in claim 27, further comprising:
a control element associated with the helical structure and extending to the proximal region of the probe body.

38. A probe, comprising:
a probe body defining a distal region, a proximal region and a longitudinal axis;
a helical structure associated with the distal region of the probe body defining proximal and distal ends and proximal and distal end diameters, the distal end diameter being less than the proximal end diameter;
an anchor member associated with the distal end of the helical structure;
a core wire formed from shape memory material including a helical portion located within the helical structure and a linear portion located within the anchor member, the helical portion defining a cross-sectional area at the proximal end of the helical structure and a cross-sectional at the distal end of the helical structure that is less than the cross-sectional area at the proximal end of the helical structure and the linear portion defining a cross-sectional area that is less than the cross-sectional area at the proximal end of the helical structure; and
a plurality of electrodes supported on the helical structure.

39. A probe as claimed in claim 38, wherein the probe body comprises a catheter body.

* * * * *